United States Patent [19]

Eaton

[11] 4,080,961

[45] Mar. 28, 1978

[54] FETUS SCALP ELECTRODE INSTRUMENT

[76] Inventor: Crosby J. Eaton, 1433 Stagecoach SE., Albuquerque, N. Mex. 87123

[21] Appl. No.: 753,280

[22] Filed: Dec. 22, 1976

[51] Int. Cl.² .............................................. A61B 5/04
[52] U.S. Cl. .............................. 128/2.06 E; 128/418; 128/DIG. 4
[58] Field of Search ............... 128/2.06 E, 2.1 E, 418, 128/419 P, DIG. 4

[56] References Cited

U.S. PATENT DOCUMENTS

| | | | |
|---|---|---|---|
| Re. 28,990 | 10/1976 | Hon et al. | 128/2.06 E |
| 3,029,820 | 4/1962 | Franklin | 128/DIG. 4 X |
| 3,120,227 | 2/1964 | Hunter, Jr. et al. | 128/2.06 E |
| 3,485,247 | 12/1969 | Ackerman | 128/418 |
| 3,750,650 | 8/1973 | Ruttgers | 128/418 |
| 3,800,784 | 4/1974 | Kiszel et al. | 128/2.06 F |
| 3,989,038 | 11/1976 | Neward | 128/2.06 E X |

OTHER PUBLICATIONS

Copland, et al., "A Simple Clinical Skin Electrode," Lancet, No. 7330, vol. 1, p. 416, 1964.
Porstmann, et al., "P Wave .. Thoracotomy," The Am. J. of Cardiology, vol. 30, July 1972, pp. 74–76.
Hon, "The Instrumentation . . . Fetal Electrocardiography," Conn. Med., May 1960, vol. 24, No. 5, p. 289.
Hon, "Instrumentation . . . and Fetal Electrocardiography," Obstetrics & Gynecology, vol. 30, No. 2, Aug. 1967, pp. 281–286.

*Primary Examiner*—Robert W. Mitchell
*Assistant Examiner*—Lee S. Cohen
*Attorney, Agent, or Firm*—William R. Woodward

[57] ABSTRACT

A cylindrical plug near the end of an insertion tube that is inserted through the mother's cervix to a position near the scalp of the fetus, carries at its forward end a pincers type electrode of fine spring wire which is held open so long as the shoulders of the electrode are confined by the insertion tube. The hooked ends of the electrode seat in notches on the end of the insertion tube so that they may open wide when the device is brought up against the scalp of the fetus. Then a drive tube fitting inside the outer tube keeps the plug from receding when the outer tube is slightly retracted, until the grasping electrode ceases to be confined by the outer tube and closes on a small portion of scalp. Thereafter, the outer tube is retracted further to free the electrode plug, after which both the drive tube and the outer tube may be removed and the electrode and its wire leads left in place to monitor the heartbeat of the fetus.

11 Claims, 9 Drawing Figures

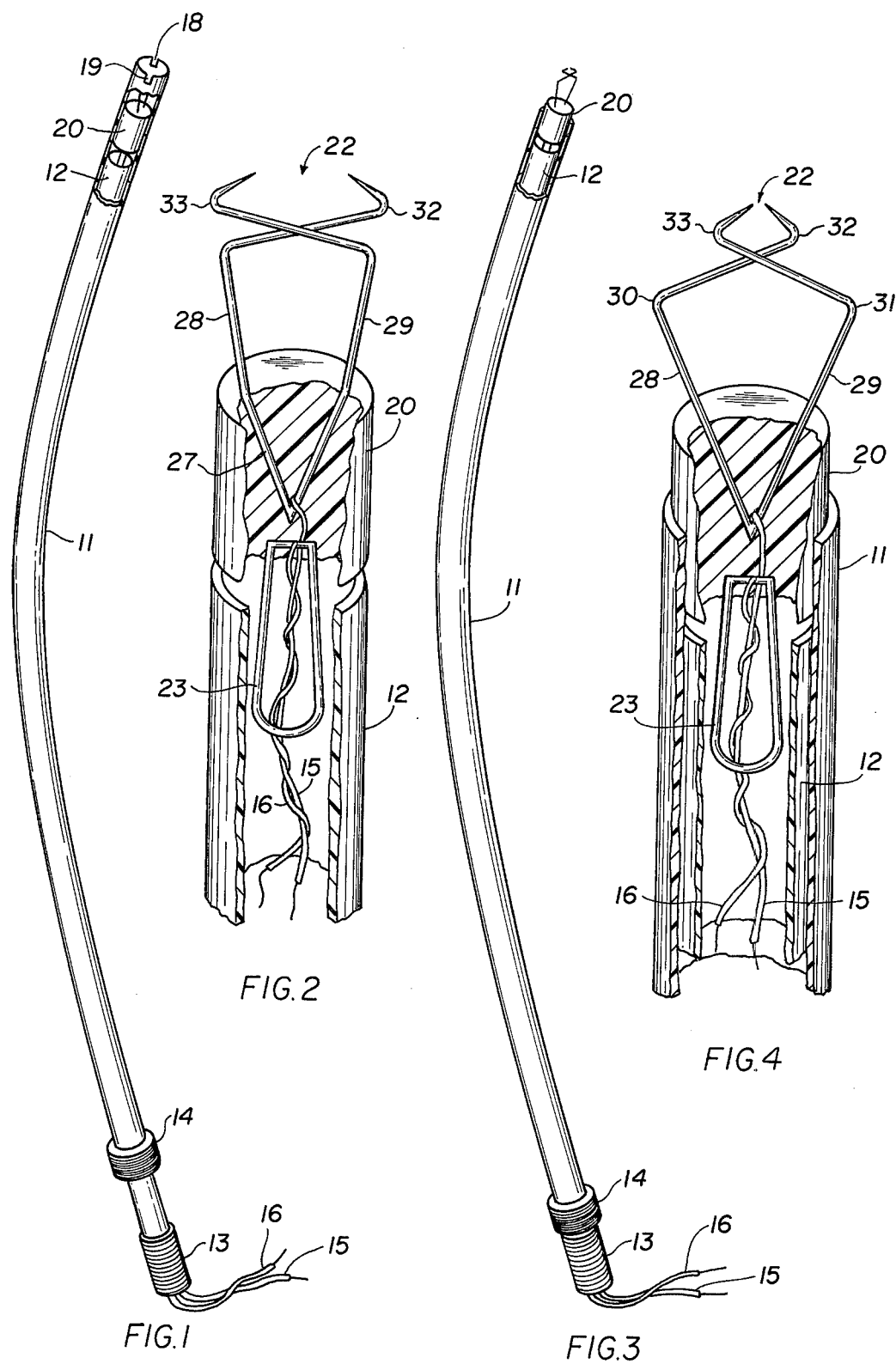

FETUS SCALP ELECTRODE INSTRUMENT

This invention relates to an electrode instrument for making contact with the scalp of a fetus for pre-natal examination purposes.

Such a device is already known which uses a helical electrode mounted on the end of a flexible drive tube which slides with a telescopic fit within an outer tube that is inserted, with the electrode retracted, into the mother's passages until it reaches the scalp of the fetus. The tubes must be able to bend at least 45° and preferably 90° in order to put the extremity through the cervix.

In order to make the known type of scalp electrode effective, when the outer tube has been placed close to the fetus scalp, the drive tube is advanced inside the outer tube until the helix electrode at its extremity makes contact with the fetal scalp. The drive tube is then rotated to engage the helix with the scalp by means of a grip at the outer end of the drive tube which enables the latter to be manipulated. A pair of wire leads passes through the drive tube and one of them connects with the helix electrode, while the end of the other is connected to a reference electrode. The two leads are brought out through the grip of the drive tube for connection to a suitable monitoring machine.

The known device above described has the disadvantage that the uncoated curled wire comes into contact with the fluid around the baby and this electrical connection with so much of the fluid interferes with the reading. Furthermore, the turning of the device to seek a better contact with the baby's scalp twists the curled electrode around and sometimes connects it to tissue of the mother rather than to the baby, with the result that the mother's heartbeat is read rather than the baby's on the monitoring device. Finally, the fragile helix has upon occasion broken while embedded within the fetal scalp tissue.

It is an object of the present invention to provide an improved fetus scalp electrode that will overcome the disadvantages of the known device.

SUMMARY OF THE INVENTION

A pincer type clip is provided which can be caused to close simply by freeing it from the constraint of the outer tube of the device, which serves as the inserter tube. The clip arms are insulated to within 0.5 to 1 millimeter from the end. The root of the clip is embedded in a plug which is advanced by an electrode drive tube that slips within the outer tube. There is also provided a counter electrode or reference electrode at least partially embedded in the plug, preferably extending back into the tube in the form of a wire loop or the like, which is found to improve the sensitivity and reliability of the device. The wire leads are connected to the grasping clip electrode and to the reference electrode at their respective portions that are embedded in the plug, so as to protect the connections against breakage. For this purpose, the plug can be simply cast around them, using a suitable synthetic resin "plastic".

The end of the outer tube is preferably notched so as to allow the open end of the clip electrode to be open wide while remaining mostly or altogether within the inserter tube during insertion.

With the electrode instrument of the present invention, the device need not be turned in order to hook a wire into the baby's scalp. The grasping action is a straight closing of pincers, at the end of the clip, moving together. In practice, after insertion of the "cocked" assembly, the electrode drive tube is first advanced, so that the clip presses against the baby's scalp. Then the outer tube is retracted, allowing the expandable part of the clip to expand, and thus close the two pincers to grasp the baby's scalp. After the electrode is thus successfully attached, the outer tube is further slipped back over the stationary drive tube to free the electrode plug from it. Then both the outer tube and the drive tube can be withdrawn from the mother's passages, leaving only the electrode plug with its clip and reference electrodes and its connection wires in place for monitoring the baby's heartbeat. The insulating coating on most of the clip reduces interference with the reading of body fluids.

The invention is further described by reference to the annexed drawings, in which:

FIG. 1 is a perspective drawing of an electrode instrument according to the invention, partly cut away at the electrode end, with the plug spaced from the electrode drive tube, to show the disposition of the major parts when the grasping electrode is in its open position;

FIG. 2 is a detail view, partly cut away, showing the electrodes, the electrode plug and the tip of the electrode drive tube when the clip is in open position as it is in the configuration of FIG. 1;

FIG. 3 is a perspective view of the electrode instrument with the tip of the outer tube partly cut away, showing the configuration of the grasping electrode in the closed position;

FIG. 4 is a detail view, partly cut away, in a manner similar to FIG. 2, showing the tip of the instrument as in FIG. 3 with the grasping electrode in its closed position;

Figure 5:
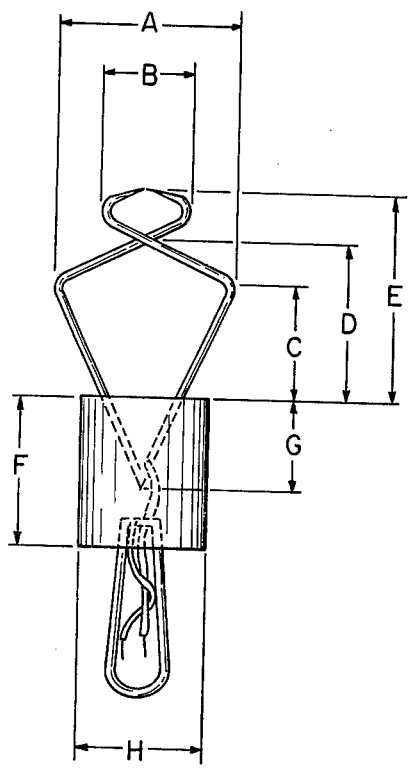
FIG. 5 is an elevation view of the electrodes and electrode plug of the grasping electrode in the closed position.

As shown in FIG. 1, the electrode drive tube 12 can be slid back and forth in the flexible outer "inserter" tube 11 by means of a grip constituted of a collar 13. The electrode leads 15 and 16 run loosely inside the drive tube 12 and protrude freely from the ends of drive tube 12 and outer (inserter) tube 11. There is a collar 14 on the outer tube 11.

Figure 7A:
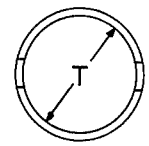
FIG. 7a is an end view and FIGS. 7b and 7c are two longitudinal sections of the end of the outer tube to show the configuration of the notches.
Figure 7B:
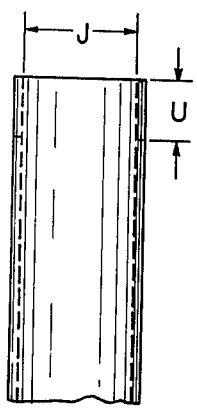
Figure 7C:
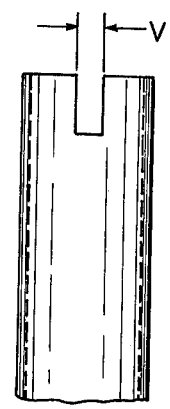

The insertion end of the outer tube 11 has notches 18 and 19 that are described further below with reference to FIG. 7. A portion of the outer tube 11 near its end has been cut away in FIG. 1 to expose the end of the electrode drive tube 12 and the electrode plug 20. The plug 20 is separate from the tube 12 rather than affixed to it and is shown spaced from the end of the tube 11 to make that fact clear. The end of the drive tube 1 can propel the plug 20 through the outer tube and out the end of the latter by pushing against the plug.

FIG. 2 is a perspective view in detail, partly cut away, of the insertion end of the tube 12, the plug 20, the grasping electrode 22, the reference electrode 23 and the connections to the electrodes. Here again, the plug is shown spaced from the end of the tube 12.

The grasping electrode 22 in the illustrated example is a clip of wire bent into a V in the middle to form a root portion 27 embedded in the plug 20. The wire is coated with thin plastic insulation coating, except that the apex of the V in the last half millimeter or so is adjacent to the ends of the wire. The electrode lead 15 is crimped or soldered to the apex of the V before the plug 20 is cast around the electrodes and their connections. The protruding arms 28 and 29 of the electrode 22 are sharply bent at 30 and 31 so as to cross, and their ends are hooked at 32 and 33 to produce a pincer configuration.

In FIG. 2 it should be understood that the arms 28 and 29, if unconstrained, continue to diverge at the same angle as the root portion 27, but that the bends 30 and 31, which are the points of maximum divergence, are constrained by the outer tube 11, as may be gathered from FIG. 1, so that the pincer ends are open as shown in FIG. 2. Actually, it is best to let the bends 30 and 31 extend into the notches 18 and 19 of the outer tube so as to open the ends of the clip as widely as possible and to insert the assembly with the electrode thus in its most "ready" position.

FIG. 3 shows the electrode instrument of the present invention after retraction of the outer tube 11 while keeping the inner drive tube 12 advanced by means of the collar grip 13, while the outer tube alone is retracted by its collar or flange grip 14. The electrode plug 20 now protrudes from the end of the outer tube 11.

FIG. 4 shows the effect of pushing the plug 20 far enough forward so that the grasping electrode 22 is no longer confined by the outer tube 11. The arms 28 and 29 are no longer bowed and have spread out to their unconstrained position, thus closing the jaws 32 and 33. The closing of the clip jaws can actually take place when the shoulders 30 and 31 of the clip reach the notches 18 and 19.

FIGS. 2 and 4 both show the electrode 23 connected to the lead 16. This electrode, of course, does not change its aspect as the plug 20 is moved forward. It consists of a loop of wire with a root portion embedded in the plug 20 both to mount the electrode 23 and to protect its connection to the lead 16.

If the electrode plug 20 is affixed to the end of the drive tube 12, instead of being separate from it as described above, it is then possible to re-open the clip electrode by advancing the outer tube 11 while pulling slightly on the drive tube by means of the collar 13, so that the outer tube 11 can advance while the drive tube does not try to advance with it. Thereafter, the entire assembly could be withdrawn or a second closing of the clip could be performed. With that type of construction, however, the advantage of being able to withdraw the outer tube and the drive tube so as to leave only the electrode plug and its electrodes and wires in place for monitoring the baby's heartbeat is no longer available. Experience shows that a good electrode connection is readily obtained with the first closing of the clip electrode, so that the advantage of being able to withdraw the tubes while leaving the electrode in place is greater than the advantage of being able to re-open the clip more easily.

Figure 6:
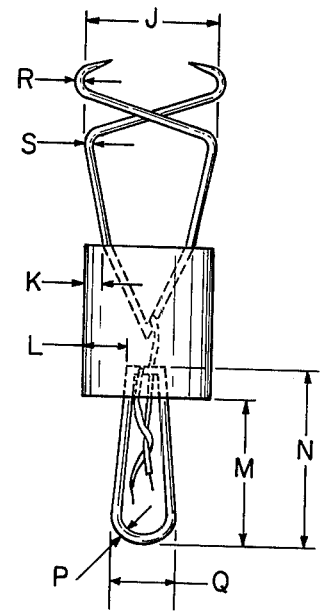
FIG. 6 is an elevation view of the electrodes and the electrode plug with the grasping electrode in the open position.

FIGS. 5 and 6 identify various dimensions of the plug and electrodes for which the preferred values are given in the following table both for inches and millimeters. FIG. 7 does the same for the outer tube and its notches.

TABLE I

| Figure | Dimension | Inch Fraction | Millimeters |
|---|---|---|---|
| | A,E | 7/16 | 14 to 15 |
| | B,G | 3/16 | 5 |
| | C,H | 1/4 | 6 |
| | D | 11/32 | 9 |

TABLE I-continued

| Figure | Dimension | Inch Fraction | Millimeters |
|---|---|---|---|
| 5 | | | |
| | F | 5/16 | 8 |
| | J | 9/32 | 7 |
| | K | 1/32 | 1 |
| | L | 3/32 | 2.5 |
| | M | 5/16 | 8 |
| 6 | N | 3/8 | 10 |
| | P,S (dia.) | 1/16 | 1.5 |
| | Q | 1/8 | 3 |
| | R (dia.) | 1/32 | 1 |
| | T | 5/16 | 8 |
| 7 | U | 3/16 | 5 |
| | V | 1/16 | 1.5 |

The wire arms of the clip 22, as noted in FIG. 6 and in the above table, are preferably of reduced diameter beyond the bends 30 and 31 since it is desired that the clip jaws that may protrude from the outer tube should be as flexible as is feasibly consistent with the scale-grasping ability. The wire of the clip must, of course, be resilient so as to provide the spring action described, but it does not need for that purpose to be of the usual and convenient circular cross-section, but may be of oval or flattened cross-section without impairment of the operation of the clip.

Although the invention has been illustrated with reference to a particular preferred illustrative embodiment, it will be understood that modifications and variations are possible within the inventive concept.

I claim:
1. A fetus scalp electrode instrument comprising:
a flexible outer tube of sufficient length to reach a fetus scalp from outside the mother's body through her passages and having a first end serving as the insertion end thereof and a second end serving as the control end thereof;
a flexible electrode drive tube telescoping within said outer tube, longer than said outer tube and having a first end serving as the insertion end thereof and a second end serving as the control end thereof, said second end of said electrode drive tube protruding from said second end of said outer tube;
a collar on said second end of said drive tube for facilitating manipulation of said electrode drive tube within said outer tube;
an electrode-carrier plug adjacent to said first end of said electrode drive tube and normally located within said outer tube and having a rear face facing the interior of the length of said drive tube and a front face facing in the opposite direction;
a grasping electrode having a root portion embedded in said electrode-carrier plug, said grasping electrode being made of spring metal wire, protruding from said front face of said plug and having opposed arms diverging, from said root portion embedded in said plug, to a maximum width which, when said electrode is not constrained by said outer tube, substantially exceeds the outer diameter of said outer tube, said opposed arms being crossed on the side of their place of maximum divergence away from said plug and being hooked over beyond the crossing so that the ends of the arms are in a pincer configuration which is closed, when said electrode is unconstrained, to a degree necessary for grasping a bit of scalp and which is open when the opposed arms are constrained at their said places of maximum divergence by being confined in said outer tube;

a reference electrode at least partly embedded in said plug, for increasing the stray field of the pair of electrodes constituted by said grasping and reference electrodes, and a pair of electrode leads running through said drive tube, each having one end respectively connected to each of said electrodes and having their other ends brought out of said drive tube as well as out of said outer tube, whereby the instrument may be inserted to approach closely the scalp of a fetus with the grasping electrode open at or near the end of the outer tube and the outer tube may then be retracted while keeping the electrode drive tube stationary or slightly advancing until the grasping electrode, which was previously confined in open position by the outer tube, is advanced relative to the outer tube to a point at which it is no longer confined and closes to grasp a portion of fetus scalp.

2. A fetus scalp electrode instrument as defined in claim 1, in which a collar is provided at said second end of said outer tube and in which said electrode-carrier plug is a body separated from and unconnected to said drive tube, whereby, after said grasping electrode is closed, both said outer tube and said drive tube may be removed to leave the electrode-carrier plug and its electrodes and lead wires in place for monitoring the heartbeat of the fetus.

3. A fetus scalp electrode instrument as defined in claim 1, in which the portion of said arms of said grasping electrode which protrude from said plug are coated with insulation, except for an extreme portion beyond a point not more than 1 millimeter from the end of each arm.

4. A fetus scalp electrode instrument as defined in claim 3, in which the insulating coating of said arms of said grasping electrode extends to a point between 0.5 and 1.0 mm from the end of each of said arms.

5. A fetus scalp electrode instrument as defined in claim 4, in which said reference electrode is in the form of a loop of metallic wire or strip extending from said rear face of said plug and of a configuration such as to fit into the interior of said electrode drive tube when said plug is located within said outer tube.

6. A fetus scalp electrode instrument as defined in claim 4, in which the inner diameter of said outer tube is approximately 7 mm, in which the grasping electrode is embedded in said electrode-carrier plug to a depth of about 5 mm and protrudes therefrom for a distance of about 1 cm, in which, further, the width of said grasping electrode at said places of maximum divergence when unconstrained is approximately 1 cm and is located at between 6 and 7 mm from said electrode-carrier plug.

7. A fetus scalp electrode instrument as defined in claim 6, in which said grasping electrode is made of round wire of a diameter of about 1.5 l mm and in which the hooked end portions of said grasping electrode are of reduced diameter.

8. A fetus scalp electrode instrument as defined in claim 3, in which said outer tube is provided with a pair of notches at diametrically opposite sides of said first end of said outer tube, said notches being of a width greater than the thickness of said arms of said grasping electrode and of a depth not less than about three times said width, whereby said grasping electrode may be further opened during the insertion operation and may be aided to close promptly upon a short withdrawal of said outer tube relative to said drive tube.

9. A fetus scalp electrode instrument as defined in claim 8, in which said electrode-carrier plug is made of a synthetic resin plastic.

10. A fetus scalp electrode instrument as defined in claim 5, in which the width of said notches is between 1.5 and 2 mm and their depth is approximately 5 mm.

11. A fetus scalp electrode instrument as defined in claim 1, in which the portion of said reference electrode which is external to said plug protrudes from said rear face of said plug.

* * * * *